US006498124B2

(12) United States Patent
Fontenot et al.

(10) Patent No.: US 6,498,124 B2
(45) Date of Patent: Dec. 24, 2002

(54) ISOLATION OF PHENYL ESTER SALTS FROM MIXTURES COMPRISING SULFOLANE

(75) Inventors: Kevin J. Fontenot, Kingsport, TN (US); David C. Attride, Jonesborough, TN (US); Keith B. Terhune, Batesville, AR (US)

(73) Assignee: Eastman Chemical Company, Kingsport, TN (US)

(*) Notice: Subject to any disclaimer, the term of this patent is extended or adjusted under 35 U.S.C. 154(b) by 26 days.

(21) Appl. No.: 09/870,641

(22) Filed: Jun. 1, 2001

(65) Prior Publication Data
US 2002/0040151 A1 Apr. 4, 2002

Related U.S. Application Data
(60) Provisional application No. 60/208,467, filed on Jun. 2, 2000.

(51) Int. Cl.$^7$ ............................................. C07C 231/24
(52) U.S. Cl. ........................................... 504/70; 584/68
(58) Field of Search ..................................... 584/68, 70

(56) References Cited

U.S. PATENT DOCUMENTS

| | | | | |
|---|---|---|---|---|
| 2,398,526 A | 4/1946 | Greenburg | ................. | 260/674 |
| 2,520,716 A | 8/1950 | Fetterly | ................. | 260/676 |
| 2,768,222 A | 10/1956 | Nixon et al. | ................. | 260/674 |
| 2,778,864 A | 1/1957 | Fenske | ................. | 260/674 |
| 4,371,470 A | 2/1983 | Matsukura et al. | ......... | 260/428 |
| 4,634,551 A | 1/1987 | Burns et al. | ................. | 252/102 |
| 4,681,695 A | 7/1987 | Divo | ................. | 252/94 |
| 4,852,989 A | 8/1989 | Burns et al. | ................. | 8/107 |
| 5,391,780 A | 2/1995 | Zima et al. | ................. | 554/69 |
| 5,391,783 A | 2/1995 | Colignon et al. | ............. | 554/98 |
| 5,393,901 A | 2/1995 | Zima et al. | ................. | 554/69 |
| 5,393,905 A | 2/1995 | Zima et al. | ................. | 554/70 |
| 5,414,099 A | 5/1995 | Heinzman et al. | ............. | 554/69 |
| 5,429,773 A | 7/1995 | Sherry et al. | ................. | 252/554 |
| 5,466,840 A | 11/1995 | Lutz et al. | ................. | 554/70 |
| 5,523,434 A | 6/1996 | Burns et al. | ................. | 554/68 |
| 5,534,195 A | 7/1996 | Chapman et al. | ............ | 510/444 |
| 5,534,196 A | 7/1996 | Chapman et al. | ...... | 252/186.27 |
| 5,650,527 A * | 7/1997 | Lutz et al. | ................. | 554/68 |
| 5,717,118 A | 2/1998 | Lutz et al. | ................. | 554/69 |

FOREIGN PATENT DOCUMENTS

| | | |
|---|---|---|
| DE | 295 349 A5 | 10/1991 |
| EP | 0 402 339 A1 | 12/1990 |
| EP | 415 472 A1 | 3/1991 |
| EP | 0 484 634 A1 | 5/1992 |
| GB | 2 249 104 A | 4/1992 |
| JP | 58-157760 | 9/1983 |
| JP | 4-130567 | 4/1992 |
| JP | 6-179648 | 6/1994 |
| JP | 6-306042 | 11/1994 |
| JP | 8-245549 | 9/1996 |
| JP | 9-110824 | 4/1997 |
| WO | WO 94/18159 | 8/1994 |
| WO | WO 94/28104 | 12/1994 |
| WO | WO 95/07883 | 3/1995 |
| WO | WO 96/16148 | 5/1996 |
| WO | WO 97/27280 | 7/1997 |
| WO | WO 99/09004 | 2/1999 |

OTHER PUBLICATIONS

Egan et al., "Separation of Xylenses Selective Solid Compound Formation with Carbon Tetrachloride", *Industrial and Engineering Chemistry*, vol. 47, No. 2, pp. 250–253. 1954.

Savitt et al., "Separation of *m*– and *p*–Cresols from Their Mixtures", *Industrial Engineering Chemistry*, vol. 44, No. 10, pp. 2428–2431, Oct. 1952.

* cited by examiner

Primary Examiner—Deborah D. Carr
(74) Attorney, Agent, or Firm—Bernard J. Graves; Michael J. Blake

(57) ABSTRACT

The invention relates to a process for isolating a phenyl ester salt from a mixture comprising sulfolane (tetrahydrothiophene-1,1-dioxide). The invention includes adjusting the temperature of a mixture comprising a phenyl ester salt and sulfolane to a temperature of about 100–150° C. This step leads to the formation of a mixture comprising a solid phenyl ester salt and sulfolane. Next, the solid phenyl ester salt is separated, while maintaining the temperature of the mixture at about 100–150° C. The invention also relates to a process that includes adding a sufficient amount of a solvent to a mixture comprising a phenyl ester salt and sulfolane to decrease the viscosity or the density of the mixture. The solvent added has a density less than about 1.20 g/cm$^3$ at 100° C. or a viscosity of less than about 2.56 centipoise at 100° C. The embodiments of the invention may be used alone or in combination. This invention may be used for the isolation of a variety of phenyl ester salts, including but not limited to sodium 4-sulfophenyl-6-[(1-oxynonyl)amino]hexanoate, sodium 4-(nonanoyloxy)benzenesulfonate, and sodium benzoyloxybenzenesulphonate.

23 Claims, No Drawings

ISOLATION OF PHENYL ESTER SALTS FROM MIXTURES COMPRISING SULFOLANE

This application claims priority under 35 U.S.C. § 119 to provisional application Ser. No. 60/208,467, filed Jun. 2, 2000, which is incorporated herein by reference.

FIELD OF THE INVENTION

The invention relates to an improved process for the isolation of phenyl ester salts from mixtures comprising sulfolane (tetrahydrothiophene-1,1-dioxide), such as a crude reaction mixture in which a phenyl ester salt is synthesized.

BACKGROUND OF THE INVENTION

Phenyl ester salts, as known in the art, have been used in detergents and as bleach activators for fabric laundering and cleaning applications. The synthesis, isolation, and purification of phenyl ester salts which are used as bleach activators, is described in U.S. Pat. Nos. 5,717,188, 5,650,527 and 5,523,434. The isolation of these phenyl ester salts is typically by techniques such as filtration or centrifugation.

In most cases, the isolation or separation steps must be done at low temperatures in order to minimize or avoid unacceptable losses of product. Centrifugation is usually done at temperatures below about 100° C. In fact, equipment rated for use above about 100° C. is difficult to obtain. However, by collecting the product at temperatures lower than about 100° C., several problems are encountered. For instance, allowing the mixture to cool to temperatures below 100° C. or to ambient temperature as described in the art, is not a satisfactory method for the isolation of many phenyl ester salts. Although filtration or centrifugation at these temperatures may be possible, the process is often too slow to be economical for large scale production. At typical reaction concentrations, the mixture becomes almost solid and cannot be readily moved for isolation. While the mixture may be made more tractable by dilution with a solvent, the result is loss of product due to increased solubility as well as a large downstream flow of solvent, which must be purified and recovered.

Another approach used to isolate detergents and bleach activators is to remove the solvent by vacuum distillation at temperatures up to 200° C. This approach is usually unsatisfactory for several reasons. Particularly for large scale production, the evaporation of the reaction solvent is expensive. Further, impurities present in the reaction mixture remain with the product, and must be removed in subsequent steps. In addition, degradation of the solvent and reaction components at the high temperatures required for drying imparts undesired color and impurities to the product. When the phenyl ester salts are made in a reaction mixture comprising sulfolane as the solvent, the degradation of the solvent is a particular problem at elevated temperatures.

Another problem associated with the isolation of phenyl ester salts from reaction mixtures occurs when the product is in the form of very fine crystals. These fine crystals rapidly form a layer upon the filter medium that is virtually impervious to the penetration of liquid, thus blinding the filter or centrifuge. When the mother liquid is viscous, these types of crystals do not settle well on sedimentation style devices. Separation is problematic when the density of the solid and the reaction solvent are similar. Slurries of fine crystals are also difficult to pump or transfer from one vessel to another at typical reaction concentrations and low temperatures.

Patents that describe techniques for the isolation of phenyl ester salts using filtration or centrifugation are discussed below, however, these techniques are typically carried out at temperatures of less than 100° C. The abstract of Japanese Patent Number 8,245,549 describes the isolation of a sulfonate from a solvent having a boiling point of less than 100° C. by centrifugation. The Abstract of Japanese Patent No. 58,157,760 describes the preparation of m-xylene-4-sulfonic acid in which centrifugation is used in product recovery after crystallization. Japanese Patent No. 4,103,567 describes the separation of alkoxybenzene sulphonic acid salts, such as sodium 5-chloro-2-(2-methoxyethoxy) benzenesulfonate, in which the product is recovered by centrifugation. The Abstract of East German Patent DD 295, 349 describes the production of basic phenolate-containing calcium sulfonates, which involves centrifuging or filtering to remove solid oil-insoluble components. U.S. Pat. No. 5,429,773 relates to the centrifugation or isolation of an alkyl ester sulfonate surfactant composition at a temperature of 10–43° C. U.S. Pat. No. 5,523,434 teaches a process for manufacture of phenol sulfonate esters of N-nonanoyl-6-aminocaproic acid, which includes centrifugation at low temperatures for isolation. U.S. Pat. No. 5,650,527 describes a method of isolation wherein the reaction solvent is removed by either evaporation, or crystallization followed by filtration.

Accordingly, what is needed is a process for the isolation of phenyl ester salts from reaction mixtures comprising sulfolane which avoids the following: high temperatures, excessive dilution with cosolvent, excessive problems with pumping or transferring the mixture, blinding of the filter medium, and undesirable solvent interactions. The invention described below answers this need.

SUMMARY OF THE INVENTION

The invention discloses an improved process for the isolation of a phenyl ester salt directly from a mixture comprising sulfolane (tetrahydrothiophene-1,1-dioxide). For example, the invention relates to the improved isolation of a phenyl ester salt from the crude reaction mixture in which the phenyl ester salt is synthesized. Any of the following steps, taken alone or in combination will improve the isolation of a phenyl ester salt from a mixture comprising sulfolane: (i) centrifugation or filtration within an optimal temperature range of about 110–150° C., (ii) addition of a solvent in amounts of about 2–4% based on weight of the crude reaction mixture to reduce the viscosity and/or density of the mother liquid prior to filtration or centrifugation, and (iii) slow cooling of the crude reaction mixture at a rate of about 8–10° C. per hour. Advantageously, the invention avoids excessive dilution with sulfolane, excessive problems with pumping the mixture, problems related to viscosity and/or density, blinding of the filter medium, or addition of large amounts of a cosolvent.

Additionally, this invention is an improvement over the practice of filtering or centrifuging at high temperatures of above 150° C., where these higher temperatures result in less complete separation of the phenyl ester salt from the solvent due to the increased solubility at that temperature. This loss of product often leads to the recycling of the filtrate or centrate with concomitant loss of efficiency, loss of product, and loss of product quality.

In a particularly preferred embodiment, this invention is used to isolate sodium 4-sulfophenyl 6-[(1-oxynonyl)-amino]hexanoate, sodium 4-(nonanoyloxy) benzenesulfonate, or sodium benzoyloxy benzenesulphonate, which are phenyl ester salts used as bleach activators.

DETAILED DESCRIPTION

Additional objects and advantages of the invention are discussed in the detailed description that follows, and will be obvious from that description, or may be learned by practice of the invention. It is to be understood that both this summary and the following detailed description are exemplary and explanatory only and are not intended to restrict the invention.

DETAILED DESCRIPTION

This invention relates to a process for the isolation of a phenyl ester salt from a mixture comprising sulfolane (tetrahydrothiophene-1,1-dioxide), such as a crude reaction mixture in which a phenyl ester salt is synthesized.

Phenyl ester salts are used as bleach activators in laundry detergents and other cleaning formulations. As shown in the reaction scheme below, the phenyl ester salt is hydrolyzed upon nucleophilic attack by a perhydroxide anion to yield a peroxy acid that acts as a bleaching agent, and a substituted phenolic anion.

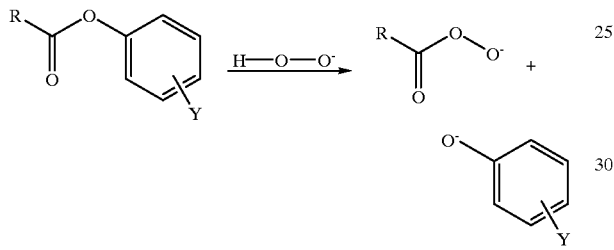

To be effective as a bleach activator, the phenyl ester salt must readily react with a perhydroxide anion to produce (activate) the corresponding peroxyacid within the length of time and at the temperature of a typical wash cycle. Employing the process of the invention improves the perhydrolysis rate of phenyl ester salts. Advantageously, then, this invention improves the efficacy of the detergent containing a phenyl ester salt bleach activator. The process of the invention can be used with any phenyl ester salt.

Exemplary phenyl ester salts, which are used as bleach activators, are described in U.S. Pat. Nos. 4,634,551; 4,852,989; 5,391,780; 5,393,905; 5,393,901; 5,414,099; 5,466,840; 5,523,434; 5,650,527; and 5,717,118; as well as in published PCT applications WO 94/18159, WO 95/07883, WO 96/16148, and WO 99/09004. These U.S. Patents and published PCT applications are incorporated herein in their entirety.

Examples of phenyl ester salts which may be isolated and recovered using the process of this invention include compounds described by formula (I) or (II) below:

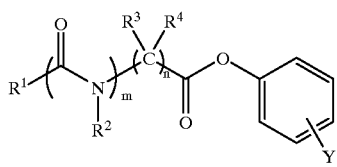

(I)

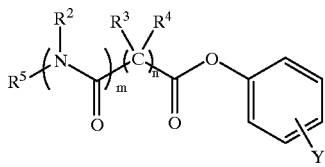

(II)

$R^1$ is selected from $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl. Preferably, $R^1$ is selected from $C_6$–$C_{10}$ alkyl, and $C_6$–$C_{10}$ aryl.

$R^2$ and $R^5$ are each independently selected from hydrogen, $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl. Alternatively, in formula II, $R^2$ and $R^5$, together with the nitrogen carrying them, form a $C_3$–$C_{10}$ heterocycle. This heterocycle may or may not contain additional heteroatoms selected from: nitrogen, oxygen, sulfur, and phosphorous. Preferably, $R^2$ is hydrogen, and $R^5$ is selected from hydrogen, $C_6$–$C_{10}$ alkyl, and $C_6$–$C_{10}$ aryl.

$R^3$ and $R^4$ are each independently selected in each instance from hydrogen, $C_1$–$C_{10}$ alkyl, $C_2$–$C_{10}$ alkenyl, $C_2$–$C_{10}$ alkynyl, $C_3$–$C_{10}$ cycloalkyl, and $C_6$–$C_{10}$ aryl. The $R^3$ and $R^4$ groups, together with the carbon carrying them, may form a $C_3$–$C_7$ cycloalkyl group. This cycloalkyl group may or may not contain heteroatoms selected from: nitrogen, oxygen, sulfur, and phosphorous. Preferably, $R^3$ and $R^4$ are independently selected in each instance from hydrogen and methyl.

The substituent Y on the phenyl ring is selected from $SO_3^-M^+$, $CO_2^-M^+$, $SO_4^-M^+$, and $N^+(R^7)_3X^-$. M represents a cation, and may be selected from hydrogen, ammonium and alkali metal atom. $R^7$ in each instance is independently a $C_1$–$C_4$ alkyl group. X is an anion, and may be selected from a halide, hydroxide, methylsulfate, or acetate ion. Preferably, Y is selected from $SO_3^-M^+$, and $CO_2^-M^+$; where M is a sodium ion.

The phenyl ring may also be further substituted with 1 to 4 other substituents. The substituents may be electron-withdrawing or electron-donating groups. The substituents may, for example, be chosen to adjust the perhydrolysis rate, to adjust the hydrophilic/hydrophobic nature of the phenyl ester salt, or to adjust the solubility of the phenyl ester salt. Possible groups include, but are not limited to, hydroxyl, halogen, $C_1$–$C_{10}$ alkyl, $C_2$–$C_{10}$ alkenyl, $C_2$–$C_{10}$ alkynyl, $C_3$–$C_{10}$ cycloalkyl, and $C_1$–$C_{10}$ alkoxy, and amino groups. When the phenyl ester salts are to be used as bleach activators, it is also desirable to have electron-withdrawing groups on the phenyl ring, to facilitate nucleophilic attack by a perhydroxide anion. In general, a substituted phenol is the preferred leaving group, however there may be other acceptable leaving groups, as will be evident to one of ordinary skill in the art. The substituted phenyl group should be sufficiently reactive for the reaction to occur within an optimum time frame, such as a wash cycle. The leaving group should also be sufficiently stable to ensure that the rate of back reaction will be negligible. However, the substituted phenyl group should not be too reactive, as this may lead to storage and stability problems in a bleaching or detergent formulation.

The value of "m" is 0 or 1 and represents the presence or absence of an amido group in the compound. Acceptable values for "n" may range from about 0 to 20, and preferred values for "n" include from about 0 to about 6.

The bleaching effectiveness of the resulting peroxy acid resulting from the phenyl ester salt may be related to its hydrophilic/hyprophobic balance. This balance, related to the choice of "m" and particularly "n", affects the solubility of the peroxy acid in water. In addition, the hydrophilic/hydrophobic balance determines which types of stains and soils that the molecule will bleach most efficiently. The presence of an amido group in the phenyl ester salt may impart certain desirable features to a bleach activator, as described in U.S. Pat. No. 4,852,989. For example, in certain circumstances, the presence of an amido group has been found to lower the vapor pressure and/or increase the melting point of the resulting peroxyacid thereby increasing the stability of the peroxyacid. Additionally, it is generally preferred to choose the value of "n" and various substituents to increase the water solubility of the peroxyacid.

For the various substituents of the phenyl ester salts of formula (I) or (II), the alkyl, alkenyl, and alkynyl groups may be straight or branched. The alkyl, alkenyl, and alkynyl groups may be optionally substituted with halogen, alkoxy groups, or water-solubilizing groups. In addition, these groups may also be substituted with various steroids, natural products and fatty acids, as known in the art.

A "water-solubilizing group" is a substituent that increases the solubility of a compound in aqueous solution. Exemplary water-solubilizing groups include, but are not limited to, quaternary amine, sulfate, sulfonate, carboxylate, phosphate, phosphonate, polyether, polyhydroxyl, boronate, and amide groups such as —$CONH_2$ and $CONHCH_3$. The water solubilizing groups may also include sulfo, sulfonamido, carbonamido, sulfamoyl, carbamoyl, hydroxyl, and salts thereof.

The $C_2$–$C_{22}$ alkenyl and $C_3$–$C_{22}$ alkynyl groups represent straight or branched chain hydrocarbon radicals containing 2 to 22 carbons in the chain and which contains at least one of a carbon—carbon double bond and/or at least one of a carbon—carbon triple bond.

The $C_3$–$C_{22}$ cycloalkyl heterocycles and rings may contain more than one degree of unsaturation and may be unsubstituted or substituted. The heterocycles and cycloalkyl rings may be optionally substituted with halogen, alkoxy groups, or water-solubilizing groups. These rings may be monocyclic, bicyclic, or polycyclic. In addition, these cycloalkyl rings may or may not contain one or more heteroatoms in the ring. Acceptable heteroatoms are selected from: oxygen, nitrogen, sulfur and phosphorus.

The $C_6$–$C_{14}$ aryl ring may be monocyclic, bicyclic, or polycyclic. In addition, the aryl ring may contain one or more heteroatoms. Appropriate heteroatoms include oxygen, nitrogen, sulfur, and phosphorus. Both the $C_3$–$C_{22}$ cycloalkyl rings and $C_6$–$C_{14}$ aryl rings may be substituted with appropriate $C_1$–$C_4$ alkylaryl, hydroxy, $C_1$–$C_4$ alkanyloxy, halogen or water-solubilizing groups. The term "aryl" includes carbocyclic aryl groups containing up to fourteen carbons, e.g., phenyl and naphthyl. The term "aryl" also includes heterocyclic aryl groups such as a 5 or 6-membered heterocyclic aromatic ring. These heterocyclic aromatic rings may also contain other heteroatoms selected from: oxygen, nitrogen, sulphur, and phosphorous. These heterocyclic aryl rings may be optionally fused to one or two phenyl rings or another 5 or 6-membered heteroaryl ring. Examples of such ring systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-[1,5-b]pyridazinyl and purinyl, benzoxazolyl, benzothiazolyl, benzimidazolyl, indolyl, and the like. The aryl groups may be substituted or unsubstituted as discussed above for the alkyl, alkenyl, and alkynyl groups.

In addition, the term "aryl" includes arylene groups. The term "arylene" defines a divalent carbocyclic aryl hydrocarbon moiety containing up to fourteen carbons, e.g., o-, m- and p-phenylene, and those substituted with one or two groups selected from $C_1$–$C_4$-alkyl, $C_1$–$C_4$-alkoxy or halogen.

In a particularly preferred embodiment, the invention relates to phenyl ester salts such as sodium 4-sulfophenyl-6-[(1-oxynonyl)amino]hexanoate, sodium 4-(nonanoyloxy) benzenesulfonate, or sodium benzoyloxy benzenesulphonate.

The phenyl ester salt to be isolated may be from a reaction product mixture with the reaction solvent (or a portion thereof) removed. Or, the starting phenyl ester salt may be the product after drying. Preferred dryers are mechanically agitated dryers capable of handling viscous material such as a Porcupine dryer from Bethlehem Corporation, Easton, Pa. or a List dryer from List Corporation, Acton, Mass. Alternatively, the starting phenyl ester salt may have been previously worked up to remove unwanted impurities, reaction by-products, solvent, color bodies, etc. The synthesis of phenyl ester salts which may be used as bleach activators, is discussed in U.S. Pat. No. 4,634,551, 4,852,989, 5,393,905, 5,523,434, 5,650,527, and WO 94/18159, which are hereby incorporated in their entirety.

In a preferred method for synthesizing phenyl ester salts, sodium 4-hydroxybenzenesulfonate, acetic anhydride and a carboxylic acid are heated in the presence of one or more catalysts to temperatures of about 155–175° C., in sulfolane as the reaction solvent. Allowing the crude reaction mixture to cool to temperatures below 100° C. or to ambient temperatures, is not a satisfactory method for isolation of the phenyl ester salt. Filtration at these lower temperatures is generally too slow to be economical for large scale production. In addition, at typical reaction concentrations, the mixture becomes almost solid and cannot be easily moved or transferred. Although the mixture may be made more tractable by diluting the mixture with a cosolvent, the disadvantages include loss of product due to solubility in the cosolvent and additional steps to recover and/or purify the solvent and cosolvent.

In an attempt to keep the mixture more manageable, filtration or centrifugation of the crude reaction mixture was attempted at temperatures above about 150° C. Although at these higher temperatures, the rate of filtration was acceptable, the result was less complete isolation of the desired product from the sulfolane due to increased solubility of the phenyl ester salt at the higher temperatures. While centrate or filtrate containing the product may be recycled to improve the yield, the product quality deteriorates and the process becomes less efficient. Thus, it is important that as much product as possible be recovered in the first pass through the isolation device.

It has been found that the following processes, taken alone or in combination, improve the isolation of a phenyl ester salt from mixtures comprising sulfolane: (i) centrifugation or filtration at temperatures within an optimal range of about 110–150° C., (ii) addition of a solvent in amounts of about 2–4% based on weight of the crude reaction mixture to reduce the viscosity and density of the mixture or slurry prior to filtration or centrifugation, and (iii) slow cooling of the crude reaction mixture, preferably at a rate of about 8–10° C. per hour.

This invention covers a process for the isolation of a phenyl ester salt from a variety of mixtures comprising sulfolane. For example, if the phenyl ester salt is formed during the course of a reaction which uses sulfolane as the reaction solvent, then the mixture may be the slurry which is formed by cooling the crude reaction mixture to a temperature where the phenyl ester salt precipitates out of solution. Additionally, the mixture may comprise a phenyl ester salt and sulfolane during a re-crystallization step, wherein the phenyl ester salt is first dissolved at an elevated temperature, and then re-crystallized by adjusting the temperature to within a temperature range of about 110–120° C.

In a preferred embodiment, the mixture is a crude reaction mixture. For instance, U.S. Pat. No. 5,650,527 describes a reaction wherein the phenyl ester salt is typically synthesized at temperatures between 155–175° C. in sulfolane. According to the first step of the process described by this invention, the temperature of the crude reaction mixture is adjusted to an optimal temperature range, of about 100–150° C., and preferably between about 110–120° C. It has been found, unexpectedly, that the isolation of the phenyl ester salt is improved when the crude reaction mixture is adjusted to this optimal temperature range. At temperatures below the optimal range, the mixture becomes too viscous to handle or separate, while at higher temperature loss of product to centrate or filtrate increases. However, within the optimal temperature range, the solid phenyl ester salt can be recovered economically and in good yields.

If the temperature is adjusted batch-wise to the optimal temperature range, by cooling, the cooling step may be effected by methods known in the art. Examples of such methods include removal of heat via an external jacket using a circulation fluid which is colder that the reactor, use of internal coils inside the reactor with a similar media, and/or adiabatic evaporation of the solvent.

Crystals of molecules of large molecular weight and geometric complexity normally grow very slowly. Hence, the rate of cooling must be carefully controlled to avoid supersaturation of the solution that leads to formation of fine crystals, poor crystal shape or inclusion of mother liquor, or co-precipitation of impurities. To avoid these unwanted events a rate of cooling of about 5 to about 15° C. is generally acceptable. Preferably the cooling rate will be about 7 to about 12° C./hr.

Further, if a mixture or slurry containing a phenyl ester salt and a solvent is at temperature below the optimal temperature range, the mixture may be adjusted, e.g. by heating, to bring the mixture within the optimal temperature range. In this situation, another solvent or additional sulfolane may optionally be added to the mixture or slurry prior to the heating step.

One factor that must be considered in all isolations is the presence of impurities in the crystallization mixture. It is well known that impurities may change both the solubility and the nature of the crystals, as well the viscosity and density of the solvent and thus their ability to be filtered or centrifuged. In general, minimizing the amount of impurities improves the ability to filter or centrifuge. Contaminants may include unreacted starting material, or undesired byproducts. For instance, centrifugation is often hampered by low conversion of starting material, which results in a higher proportion of impurities. For a laboratory-scale reaction, the conversion is generally better controlled and consequently the separation results were normally better than what was experienced in a large-scale pilot plant.

The concentration of the phenyl ester salt in the mixture or slurry fed to the isolation device is preferably in the range of about 18–25 weight percent, although much wider concentration ranges, in the range of from about 10 to about 40 weight percent of solids are within the scope of the invention. If a crude reaction mixture is used, solvent may optionally be added to bring the concentration of the phenyl ester salt to the desired concentration. However, the temperature of the mixture comprising the phenyl ester salt should be adjusted or maintained within the optimal temperature range.

The step wherein the solid phenyl ester salt is separated from the mixture should be carried out while maintaining the temperature of the mixture within the optimal temperature range, of about 100–150° C. The separating step may be carried out by any method known in the art, including but not limited to, filtration and centrifugation.

If filtering is used, the filter should be preheated to the optimal temperature range and well insulated to avoid temperature loss during the filtration. Further, for large applications, the filtering process can be effected in batch or continuous mode. The filter media should be selected to withstand the temperature requirements, provide sufficient wettability, avoid chemical degradation, and provide fast filtration with good yields. The pore size of the media must be selected only after the crystal size distribution is available. Examples of batch filters include but are not limited to a pressure nutsche, a vacuum nutsche, a plate and frame filter press, and an auto-filter dryer. The continuous equipment examples include a rotary vacuum filter, a rotary pressure filter, a candle filter, and a belt filter. In each of these applications it is advantageous to prewet the filter media with hot sulfolane. Since filtration rate decreases with increasing cake thickness, careful control of the cake depth is necessary. Production of large lumps during discharge of the cake from the filter causes unnecessary difficulties in further processing. To avoid this, the cake should be discharged while hot.

When centrifugation is used to isolate the phenyl ester salt, the centrifugation mechanism employed can be either a sedimentation centrifuge or a filtration centrifuge. In a filtering centrifuge, the cake is produced on a perforate basket that allows the mother liquor to flow through the perforations, in a manner similar to cake filtration. Here, however, the centrifugal force is the driving force for separation. Sedimentation style centrifuges depend on the differences in density between the solids and the liquid to provide a means to settle the solids. The solids or the liquid can then be removed to obtain the other phase.

Regardless of the type of centrifuge used, the unit should optimally be preheated to the desired temperature and maintained at this temperature during the entire process. For filtering style centrifuges, prewetting of the filter media with sulfolane is desirable, but not necessary. Centrifugation can be performed in either a batch wise or continuous manner. Batch centrifuges have limited capacity in solids collection. Examples of filtering batch centrifuges that could be used to isolate phenyl ester salts include a vertical or horizontal basket centrifuge and an inverting basket centrifuge. Continuous filtering centrifuges usually have stricter requirements in terms of crystal size. Examples of these centrifuges include a pusher and a screen-bowl centrifuge. Sedimentation style centrifuges can operate in batch or continuous mode as well. Examples of the former include the tubular bowl and the disc centrifuge, while examples of the later include the opening bowl disc stack and the solid-bowl continuous-scroll decanter. Here the batch centrifuges provide more flexibility in residence times and g-force whereas the continuous units provide much greater capacity and are much less labor intensive. Regardless of the device used, it must optimally be designed to allow operation within the desired temperature range with little ambient heat loss. The ability to flush with fresh solvent may also be desirable.

It has also been found that the addition of a solvent to a mixture comprising a phenyl ester salt and sulfolane will reduce the viscosity and/or density of the mixture, when the density or viscosity of the solvent added is lower than that of sulfolane. For example, a density of less than about 1.20 g/cm$^3$ at 100° C. or a viscosity of less than about 2.56 centipoise at 100° C. is required. Additionally, this solvent should be selected such that is not reactive with any of the components in the reaction mixture, does not hydrolyze the product, and has a density and viscosity lower than sulfolane. Suitable solvents may be selected from a variety of acids, alkanes, ketones, alcohols, and other organic acids. Preferred solvents are propionic acid, pentanol, n-butyl alcohol, methylpropyl ketone, methyl isobutyl ketone, methyl isopropyl ketone, and heptane. The preferred boiling point of the solvent is above 90° C., and more preferably the boiling point of the solvent is above 100° C.

Exemplary solvents used in this step, include a variety carboxylic acids. Acceptable forms of the carboxylic acid, include aqueous solutions of the acid, and concentrated/glacial forms of the acid. According to the process described in this invention, it has been observed that the addition of acid to the reaction mixture improves handling characteristics such as filterability or centrifugeability, which results in improved isolation of the phenyl ester salt.

In a highly preferred embodiment, acetic acid is used. The acid appears to reduce the viscosity and density of the mixture. The amount of acid added to the mixture comprising the phenyl ester salt and sulfolane should generally be below about 10% and preferably between about 2% and about 4%, based upon the weight of the reaction mixture. The addition of excessive amounts of acid should be avoided, as this may lead to decomposition of the phenyl ester salt, resulting in lower yields.

The acetic acid should be added at a temperature at which decomposition is unlikely to occur. For example, in the production of sodium 4-sulfophenyl 6-[(1-oxynonyl)-amino]hexanoate, if the acid is added at temperatures above 150° C., there is observed a significant amount of decomposition. Because many of the other phenyl ester salts in the art contain functionality such as ester or amide groups, decomposition at higher temperatures under acidic conditions may also be a concern. Preferably, this step is carried out while maintaining the temperature of the reaction mixture within the optimal temperature range of about 100–150° C.

To avoid decomposition of the product, it is necessary to isolate the phenyl ester salt prior to any substantial decomposition of the phenyl ester salt. Therefore, the acetic acid may optionally be added immediately prior to the collecting step, in order to avoid loss of yield due to degradation of product over prolonged times. Typically, the product is collected within about an hour of the addition of the acetic acid.

The step of separating the solid phenyl ester salt from the mixture may be accomplished by the methods discussed previously, such as filtration or centrifugation. This step is carried out while maintaining the temperature of the mixture comprising the phenyl ester salt and sulfolane within the optimal temperature range.

It has also been found that the isolation of a phenyl ester salt from a mixture may be improved by controlling the rate at which the reaction mixture is cooled during crystallization. For instance, the isolation of phenyl ester salts from reaction mixtures is difficult when the product is in the form of fine crystals. To aid in the separation, the cooling of the crude reaction mixture to the separation temperature should be controlled to allow maximum growth of the crystals. If the reaction mixture is cooled too rapidly, small crystals are formed which can blind the filter or centrifuge. Accordingly, the cooling of the mixture should be as slow as is consistent with good economics. For batch processes this is done by reducing the rate at which the temperature is lowered in the vessel. In order to cool the mixture "slower" in continuous processes, the residence time in the vessels must be increased by increasing the number of stages or increasing the vessel size.

Each of the embodiments of the processes described by this invention may be used individually or in combination, to improve the isolation of a phenyl ester salt.

In a particularly preferred embodiment, this invention relates to processes to improve the isolation of phenyl ester salts including sodium 4-sulfophenyl-6-[(1-oxynonyl)amino]hexanoate, sodium 4-(nonanoyloxy)benzenesulfonate, or sodium benzoyloxy benzenesulphonate. Although, as discussed above, the processes of this invention may be used to improve the isolation of a broad range of phenyl ester salts.

EXAMPLES

The practice of the invention is disclosed in the following examples, which should not be construed to limit the invention in any way. The crude phenyl ester salt used in these examples is sodium 4-sulfophenyl-6-[(1-oxynonyl)-amino] hexanoate which has been prepared from the reaction of sodium 4-hydroxybenzenesulfonate, acetic anhydride, and nonanamidohexanoic acid in sulfolane with sodium acetate, imidazole, and/or caustic as catalysts(s). This process is described in U.S. Pat. Nos. 5,414,099 and 5,650,527 which are incorporated in their entirety. For a discussion of filtration and solid/liquid separation see T. Christopher Dickenson, Filters and Filtration Handbook, 4$^{th}$ ed.; Elsevier, N.Y. 1997 and Purchas and Wakeman, Eds.; Solid/Liquid Separation Equipment Scale-up; Uplands Press Ltd, London 1977; which are both incorporated in their entirety.

I. Examples 1–6

Filtration

In examples 1–6, sodium 4-sulfophenyl 6-[(1-oxynonyl)-amino]hexanoate was isolated by filtration on a laboratory scale. The results of Examples 1–6 are summarized in Table 1 and Table 2.

The theory of batch filtration is explained in Purchas and Wakeman, Eds.; Solid/Liquid Separation Equipment Scale-up; Uplands Press Ltd., London 1977. In summary, $$Q = \frac{dv}{dt} = \frac{A^2 P_T}{\mu(\alpha \omega V + A R_M)}$$

where
   Q=the flow rate of filtrate
   V=the volume of filtrate collected at a given time (t)
   A=the cross sectional area of the filter
   $P_T$=the pressure drop across the filter
   $\mu$=the viscosity of the filtrate at the temperature filtered
   $\alpha$=cake resistance ω=the concentration of the solids in the slurry, and $R_M$=is the resistance of the filter media (usually neglected)

At constant pressure this can be integrated to achieve $t/V = K_1 V + K_2$, where $K_1 = w/2A^2 P_T$, and $K_2 = R_M/AP_T$ Therefore, in a plot of the value of t/V versus V for a given filtration, the slope of the best fitting line will be $K_1$. From the value of $K_1$ we can obtain the cake resistance, α. The value of cake resistance can be used to determine viability of the process and to compare the efficiency of filtration at different operating conditions.

Examples 4 and 5 are not directly comparable to Examples 1–3. The material centrifuged in Examples 4 and 5 was created from a batch where the solvent that was used in the reaction was recycled centrate, i.e. the centrate from Example 3 was recycled as solvent for Example 4 and the centrate for Example 4 was recycled as solvent for Example 5. Consequently, the level of I purities and fines in the material increases as we go from Example 3 to Example 4 to Example 5. Although separation is feasible in these cases, it is not optimal. The cake contain more solvent and more impurities. Hence, a demonstration of the need for high conversion.

For Example 3, the control of the feed rate was manual. The operator had to closely watch the amount of material on the centrifuge. If the feed rate was too fast, the material would spill over into the centrate and lower the recovery. It is likely that this was the case. Also the temperature of the centrifuge was not in the preferred temperature range of 110–120° C.

From previous lab-work, it was known that the phenyl ester salt would not filter below 100° C., and so this was not attempted at the pilot scale. However, it was initially attempted to feed the centrifuge without preheating the cloth inside with hot solvent prior to feeding the slurry. The cloth quickly blinded over and recovery was extremely low. Temperatures above 150° C. were not tried due to (1) known effects on yield, (2) the difficulty of getting the centrifuge heated to that temperature.

Examples 1A and 1B

Examples 1A and 1B illustrate that sodium 4-sulfophenyl 6-[(1-oxynonyl)-amino]hexanoate can be isolated by filtration, without dilution of the mixture at 108° C., given good crystallization of the phenyl ester salt for growth of nominal size crystals. Approximately 140 grams of pure dry sodium 4-sulfophenyl 6-[(1-oxynonyl)-amino]hexanoate, was charged to a vessel containing 1034 grams of sulfolane. The only impurities found were 0.34% sodium phenolsulphonate and 0.12% nonanoic acid. This mixture was heated until all the sodium 4-sulfophenyl 6-[(1-oxynonyl)-amino] hexanoate went into solution.

In Example 1A, the solution was cooled down to 108° C. and 550 grams of the slurry was filtered on a preheated coarse-fritted glass filter. It took about 4 minutes to gather 460 grams of filtrate and 88 grams of sulfolane wet cake. The crystals produced were uniformly shaped at around 30 to 40 microns.

In Example 1B, the solution was cooled to 90° C. and 555 grams of the slurry was filtered on a preheated coarse-fritted glass filter. It took over ten minutes to gather 406 g of filtrate.

A comparison of Examples 1A and 1B demonstrate the effect of temperature on the time required for filtration. The time for filtration is reduced by a factor of greater than two when the temperature is within the optimal temperature range.

Example 2

A nitrogen purged 3-liter geometrically scaled glass laboratory reactor was charged with the following: 1004 g sulfolane, 171.8 g of nonanamidohexanoic acid (of which 6 g was nonanoic acid), 124.2 g of sodium phenylsulfonate, 2.63 g of sodium acetate, and 2.18 g of imidazole. This mixture was degassed at 80° C. and then heated to 140° C. Once at this temperature, 74.6 g of acetic anhydride was added over 72 minutes. The system was then placed under vacuum to remove the acetic acid produced. Once boiling ceased at 140° C. and 60–75 mm Hg, the temperature was increased to 170° C. and the vacuum slowly lowered. The vacuum distillation continued until 620 total grams of material in total was removed from the reactor. Fresh sulfolane (840 grams) was added back to the reactor. The mixture was held at 170° C. for 15 minutes and then cooled down to 110° C. at 7.5° C./hr.

A 439 g aliquot of this mixture (containing about 17 wt. % sodium 4-sulfophenyl 6-[(1-oxynonyl)-amino]hexanoate in sulfolane) was filtered on a preheated coarse-fritted glass filter at 20 mm Hg vacuum. In 137 seconds, 271 g of filtrate were collected. The filtrate contained 0.6% sodium 4-sulfophenyl 6-[(1-oxynonyl)-amino]hexanoate. The cake was washed twice with 60 grams of sulfolane which had been heated to 120° C. The final washed cake was 114 grams and analyzed as containing 47% moisture. The sodium 4-sulfophenyl 6-[(1-oxynonyl)-amino]hexanoate in the cake represented about 97% sodium 4-sulfophenyl 6-[(1-oxynonyl)-amino]hexanoate on a dry basis. The loss of sodium 4-sulfophenyl 6-[(1-oxynonyl)-amino]hexanoate in the filtrate represented only 6% of the sodium 4-sulfophenyl 6-[(1-oxynonyl)-amino]hexanoate produced in the reaction. Conversion of the nonanamidohexanoic acid to sodium 4-sulfophenyl 6-[(1-oxynonyl)-amino]hexanoate was calculated to be 94% at the point of filtration.

Example 3

All the conditions of Example 2 were followed except batch temperatures were kept below 155° C. during the vacuum distillation portion of the reaction. Also, only 680 grams of material was removed by vacuum distillation, and only 810 grams of sulfolane were added back to the reactor before cooling down. The batch was cooled from 152° C. to 100 C over 2 hours. A 350 g portion of the slurry (containing about 18 wt % sodium 4-sulfophenyl 6-[(1-oxynonyl)-amino]hexanoate) was filtered in a manner similar to the above example. Approximately 220 g of filtrate containing 0.5% sodium 4-sulfophenyl 6-[(1-oxynonyl)-amino] hexanoate was collected in 240 seconds. The cake was washed once with 100 g sulfolane at a temperature of 105° C. A 93 gram cake containing 43% sodium 4-sulfophenyl 6-[(1-oxynonyl)-amino]hexanoate and 50% sulfolane was obtained. The overall yield of the sodium 4-sulfophenyl 6-[(1-oxynonyl)-amino]hexanoate for the filtration was 90%.

A comparison of Example 3 with Example 2 shows the effect of a slow rate of cooling on the cake resistance. Cooling the reaction mixture at 7.5° C. versus 26° C. results in an improvement in cake resistance of almost an order of magnitude.

Example 4

The remaining slurry from Example 3 was cooled to 90° C. and a filtration attempted again on a preheated filter. This time it took 8 minutes to filter 350 grams and collect 205 grams of filtrate. The cake was washed once and yielded a final product of 42% sodium 4-sulfophenyl 6-[(1-oxynonyl)-amino]hexanoate and 53% sulfolane. The overall yield of sodium 4-sulfophenyl 6-[(1-oxynonyl)-amino]hexanoate was 94% while the filtrate contained 0.4% sodium 4-sulfophenyl 6-[(1-oxynonyl)-amino]hexanoate.

A comparison of Example 4 with Example 3 shows the effect of the filtration temperature on the cake resistance. By filtering at 100° C. instead of 90° C., the cake resistance is reduced by over a factor of two.

Example 5

Example 5 is an attempt to reheat and crystallize a slurry containing phenyl ester sulfonate without acid dilution. Approximately 866 grams of a slurry made from a reaction mixture was charged to a reactor. This material was heated to 155° C. and cooled to 110° C. at a rate of 12° C./hour. Agitation during the cooling step was adequate to ensure good heat transfer.

Once the mixture was at 110° C., 140 g of fresh sulfolane was added as diluent. Approximately 300 g of this material were filtered on a preheated coarse-fritted glass filter. The mixture took about 5 minutes to filter and 175 grams of filtrate were collected. The cake (114 grams) was analyzed to be 71% sulfolane and 27.1% sodium 4-sulfophenyl 6-[(1-oxynonyl)-amino]hexanoate, while the filtrate contained 2% sodium 4-sulfophenyl 6-[(1-oxynonyl)-amino]hexanoate.

Example 6A–6C

Examples 6A to 6C illustrate that dilution with acetic acid enhances the filtration rate over the previous example. Approximately 2300 g of a slurry produced from a reaction mixture containing sodium 4-sulfophenyl 6-[(1-oxynonyl)-amino]hexanoate in sulfolane (approximately 78% amido acid conversion by assay) was heated to 100° C. It was charged to a jacketed 3-liter reactor equipped with agitator and baffles, which had been preheated to 150° C. The initial assay of the starting material is shown in Table 2. The mixture was heated to 155° C. and held for 1 hr, then cooled at a rate of 15° C./hr to 110° C. To this slurry, 245 g of sulfolane and 101.5 g of acetic acid were added, increasing the level of acetic acid in the slurry to 4%. The material was held for 50 minutes while the temperature increased to 116° C.

In Example 6A, a 300-g aliquot of this slurry, at 116° C., was filtered on a heated coarse-fritted glass filter with 20 mmHg vacuum. The 223 g of filtrate were collected in 61 seconds, leaving a cake of 76 g. The filtrate was analyzed to be 3.0 wt % sodium 4-sulfophenyl 6-[(1-oxynonyl)-amino] hexanoate and the wet unwashed cake contained 59% sulfolane with total moisture of 62%.

In Example 6B, a separate sample of the same slurry was cooled to 107° C. and filtered as before. This sample (250 g) filtered in 146 seconds and gave 170 g of filtrate and 65.5 g of wet cake. The wet cake was found to contain 28.5% sodium 4-sulfophenyl 6-[(1-oxynonyl)-amino]hexanoate and 56.4% sulfolane; the filtrate contained 2.3% sodium 4-sulfophenyl 6-[(1-oxynonyl)-amino]hexanoate and 5.2% acetic acid. The remaining composition numbers are shown in the table above.

In Example 6C, an additional 75 g of acetic acid was added to the remaining original slurry to raise the concentration of acetic acid to about 10%. After 60 minutes, 262 grams of this material were filtered at 110° C. to yield 204 g of filtrate and 48 g of cake. The filtration time was 142 seconds. The wet unwashed cake was analyzed to contain 24.8% sodium 4-sulfophenyl 6-[(1-oxynonyl)-amino] hexanoate and 57.8% sulfolane, while the filtrate contained 4.5% of sodium 4-sulfophenyl 6-[(1-oxynonyl)-amino] hexanoate. By the end of the experiment, the slurry had degraded to 8.2% sodium 4-sulfophenyl 6-[(1-oxynonyl)-amino]hexanoate due to the equilibrium of the reaction.

As the examples above illustrate, the product from the preparation of sodium 4-sulfophenyl 6-[(1-oxynonyl)-amino]hexanoate in sulfolane may be recovered readily by centrifugation or filtration at temperatures in the range 107–125° C. At lower temperatures, particularly below 100° C., the mixture became too thick to allow effective isolation of the phenyl ester salt from the mixture.

TABLE 1

Examples 1–6: Filtration

| Example | 1A | 1B | 2 | 3 | 4 | 5 | 6A | 6B | 6C |
| --- | --- | --- | --- | --- | --- | --- | --- | --- | --- |
| Cooled From Temperature (° C.) |  | 108 | 170 | 152 |  | 155 | 155 | 155 | 155 |
| To Temp (° C.) | 108 | 90 | 110 | 100 |  | 110 | 110 |  |  |
| At a rate of (° C./hr) |  |  | 7.5 | 26 |  | 12 | 15 |  |  |
| Amount of Additional Sulfolane Added (g) | — | — | 840 | 810 |  | 140 | 245 |  |  |
| Amount of Acetic Acid(g) Added | — | — | — | — |  |  | 101.5 | 105.4 | 101.5 |
| Temperature (° C.) | 108 | 90 | 110 | 100 | 90 | 110 | 116 | 107 | 110 |
| Amount Filtered (g) | 550 | 555 | 439 | 348 | 350 | 295 | 308 | 250 | 262 |
| Amount Filtrate Collected (g) | 460 | 406 | 271 | 220 | 205 | 175 | 223 | 170 | 204 |
| Time for Filtration (sec) | 240 | 660 | 137 | 240 | 480 | 300 | 61 | 146 | 142 |
| Vacuum for Filtration (mm Hg) | 10–15 | 20 | 20 | 20 | 20 | 20 | 20 | 20 | 20 |
| Filter Area (cm$^2$) | 49 | 49 | 49 | 49 | 49 | 49 | 49 | 49 | 49 |
| Cake Resistance in ($10^{10}$ ft/lbm) | N/a | N/a | 0.34 | 2.5 | 5.9 | 6.2 | 0.90 | 1.3 | 1.46 |
| sulfolane in cake (g) | 38.6 | 43.5 | 31.3 | 50 | 53 | 71 | 58.6 | 56.4 | 57.8 |
| phenyl ester salt in cake (wt. %) | 56.1 | 50.3 | 48.5 | 43 | 42 | 27 | 26.7 | 28.5 | 24.5 |
| number of sulfolane washes | — | — | 2–60 | 1–100 | 1–100 | — | — | — | — |
| overall yield (wt %): | 96 | 98.5 | 94.4 | 90 | 94 | 90.0 | 81.3 | 85.5 | 71.1 |
| phenyl ester salt in filtrate (wt %) |  | 0.23 | 0.6 | 0.52 | 0.36 | 1.97 | 3.0 | 2.3 | 4.5 |

TABLE 2

Analytical Results for Examples 5 and 6 (in weight %)

| Example | I | II | III | IV | V | VI | VII | VIII |
|---|---|---|---|---|---|---|---|---|
| Example 5 Starting Material | 13.1 | 0.78 | 0.90 | 1.65 | 1.10 | 0.44 | 1.21 | 76.1 |
| Example 5 Cake | 27.1 | 1.0 | 1.47 | 3.12 | 0.53 | 0.53 | 1.13 | 71.3 |
| Example 6 Starting Material | 12.4 | 1.42 | 0.97 | 1.75 | 2.06 | 0.67 | 3.13 | 75.2 |
| Example 6A Cake | 26.7 | 1.38 | 0.75 | 2.06 | 1.15 | 0.48 | 2.74 | 58.6 |
| Example 6A Filtrate | 3.0 | 0.72 | 0.61 | 1.09 | 1.40 | 0.34 | 1.93 | 81.7 |
| Example 6B Cake | 28.5 | 1.39 | 0.73 | 2.23 | 1.24 | 0.45 | 3.08 | 56.4 |
| Example 6B Filtrate | 2.3 | 0.64 | 0.54 | 1.13 | 1.52 | 0.34 | 2.17 | 80.6 |
| Example 6C Cake | 24.8 | 0.78 | 0.52 | 1.59 | 1.36 | 0.35 | 2.37 | 57.8 |
| Example 6C Filtrate | 4.5 | 0.72 | 0.49 | 1.20 | 1.48 | 0.36 | 2.31 | 70.9 |

I. sodium 4-sulfophenyl 6-[(1-oxynonyl)-amino] hexanoate
II. sodium 4-(nonanoyloxy) benzenesulfonate
III. di-sodium 4-sulfophenyl 6-[(1-oxynonyl)-amino] hexanoate
IV. di-nonanamidohexanoic acid
V. nonanamidohexanoic acid
VI. 4-hydroxybenzenesulfonate
VII. sodium acetyloxybenzene sulfonate
VIII. sulfolane

II. Examples 7–11

Batchwise Centrifugation

In each of Examples 7–9, crude reaction mixtures comprising sulfolane as the solvent, were diluted with sulfolane to produce a slurry comprising solid phenyl ester salt in sulfolane. This slurry was centrifuged on a Tolhurst 30-inch (762 mm) basket centrifuge operating at 1000 rpm. The material was fed to the preheated basket as quickly as possible while trying to avoid spill over. In examples 10 and 11, the centrate produced in Example 9 was recycled. Results are summarized in Table 3.

The feed solid is the amount of solid phenyl ester salt which is added to the centrifuge in the form of a mixture or a slurry in sulfolane. The centrifuge temperature is maintained throughout the entire centrifugation process. The amount of sulfolane in the wet cake was measured by gas chromatography analysis. The loss of the phenyl ester salt to the centrate was determined by high pressure liquid chromatography (HPLC) analysis.

As shown in Table 3, when the temperature of the mixture is in the range of about 100–150° C., optimal results are obtained, as determined by a lower amount of sulfolane in the wet cake, and a reduced loss of phenyl ester salt to the centrate.

For Example 9, the control of the feed rate was manual. The operator had to closely watch the amount of material on the centrifuge. If the feed rate was too fast, the material would spill over into the centrate and lower the recovery. It is likely that this was the case. Also the temperature of the centrifuge was not in the preferred temperature range of 110–120° C.

Please note that Examples 10 and 11 are not directly comparable to Examples 7–9. The material centrifuged in Examples 10 and 11 was created from a batch where the solvent that was used in the reaction was recycled centrate, i.e. the centrate from Example 10 was recycled as solvent for Example 11. Consequently, the level of impurities and fines in the material increases as we go from Example 9 to Example 10 to Example 11. Although separation is feasible in these cases, it is not optimal. The cakes contain more solvent and more impurities. Hence, a demonstration of the need for high conversion in the reactors to minimize the level of impurities.

From the previous lab work, it was found that the phenyl ester salts would not filter below 100° C., and so this was not attempted at the pilot scale. However, it was initially attempted to feed the centrifuge without preheating the cloth inside with hot solvent prior to feeding the slurry. The cloth quickly blinded over and recovery was extremely low.

TABLE 3

Examples 7–11: Batchwise Centrifugation

| Example | | 7 | 8 | 9 | 10 | 11 |
|---|---|---|---|---|---|---|
| Feel Solids (wt %) | | 16.3 | 16.7 | 18.5 | 20.0 | 16.1 |
| Acetic acid (wt %) | | 0.2 | 0.4 | 0.4 | 0.6 | 0.3 |
| Centrifuge temperature (° C.) | | 115 | 110 | 107 | 120 | 113 |
| Average cooling rate (° C./hr) | | 7 | 10 | 12 | 10.5 | 8.5 |
| Feed rate: | | Manual | Manual | Manual | Manual | Manual |
| Phenyl ester salt in cake (wt %): | Mean Range | 57.3 | 59.1 | 50.4 | 56.7 | 34.1 |
| Solids in cake (wt %): | Mean Range | 62.6 | 66.5 | 59.0 | 63.1 | 44.0 |
| Sulfolane in cake (wt %) | Mean | 37 | 35 | 40 | 29 | 52 |
| Recovery of phenyl ester salt (wt %): | Mean Range | 93.3 | 48.1 | 72.9 | 90.3 | 90.8 |
| phenyl ester salt in centrate (wt %): | Mean Range | 1.2 | 7.8 | 5.7 | 2.1 | 1.5 |

III. Examples 12–15

Continuous Decanter Centrifugation

In previous Examples 6–9, a Bird HP-150 decanter centrifuge was used, and in Examples 7–11, basket centrifugation was used. In Examples 12–15, however, the principal of separation is sedimentation. The bowl (12.3 inch (312 mm) bowl length) had a "beach" portion, that was 4.5 inches (115 mm) in horizontal length with a 10° angle. The scroll was a double lead, 1.96 in/rev pitch and the pool height was 0.53 inch (13.5 mm). The centrifuge was steam traced and insulated, and operated between 2000 and 3000 G's. The scroll speed is mechanically set as a function of the bowl speed.

In Example 12, 0.3% acetic acid was added, and in Examples 13–15, acetic acid was added, in the amounts shown, to the feed mixture to aid in the separation via reduction of the mother liquor density and viscosity. The results are summarized in Table 4.

The amount of "Feed Acetic Acid" is the weight percentage of acetic acid in the mixture, based on the total weight of the mixture comprising the phenyl ester salt and sulfolane. The amount of "Feed Solids" is the weight percent of the solids which are in the mixture.

In Table 4, the addition of acid results in higher recovery of phenyl ester salt, and lower loss of phenyl ester salt to centrate, as shown by comparison of Example 12 with Examples 13–15.

TABLE 4

Examples 12–15: Continuous Decanter Centrifugation

| Example | | 12 | 13 | 14 | 15 |
|---|---|---|---|---|---|
| Feed Solids | | 14.4 | 16.3 | 16.0 | 25.1 |
| Acetic acid (wt %) | | 0.3 | 5.1 | 3.2 | 4.3 |
| Centrifuge temperature (° C.) | | 120 | 110 | 125 | 122 |
| Average cooling rate (° C./hr) | | 7 | 7 | 6 | 8 |
| Feed rate: | | 281–500 | 200–940 | 470–1060 | 200–1170 |
| phenyl ester salt | Mean | 30 | 28.8 | 21.2 | 31.8 |
| in cake: | Range | 27–31 | 27–32 | 20–23 | 27–35 |
| Solids in cake: | Mean | 36 | 33.3 | 46.2 | 46.0 |
| | Range | 33–38 | 32–36 | 43–50 | 41–50 |
| Sulfolane in wet cake | Mean | 58 | 56 | 45 | 48 |
| Recovery of phenyl | Mean | 45.6 | 50.2 | 50.6 | 62.0 |
| ester salt: | Range | | 15–76 | 40–61 | 43–80 |
| phenyl ester salt | Mean | 7.4 | 8.8 | 5.3 | 12.1 |
| in centrate: | Range | | 5.1–12.5 | 4.7–6.1 | 7.7–15.1 |

IV. Examples 16–18

Continuous Vertical Bowl Centrifugation

The 6-inch decanter centrifuge used in previous Examples 12–15 has a short residence time for the centrate. Using a decanter centrifuge with a longer residence time for both the solids and the centrate was found to generally give both better product recovery and a drier cake as indicated in Examples 16–19. In the following examples, carried out on a pilot plant scale, a Sharples P850 vertical solid-bowl decanter was used for centrifugation. This centrifuge has a total bowl length of 20 inch (508 mm), with a beach horizontal length of 3.82 inch (97 mm) at a 10° angle. The unit has a fixed weir height which can be adjusted via internal adjustments when the unit was down. The unit was traced with 90 psi steam and insulated to maintain process temperatures during centrifugation. Feed entered the bowl through a tube that shot the feed at a deflector plate.

Example 16

A slurry consisting of sodium 4-sulfophenyl 6-[(1-oxynonyl)-amino]hexanoate and reaction impurities in sulfolane was fed to the centrifuge. The unit was run at 2700 G's of centrifugal force with a 12.3 rpm scroll differential speed. Proper momentum of the feed onto the deflector plate was not being achieved at a feed rate of 450 lb/hr (3.4 kg/min). At 130° C., a slurry consisting of 10.9% sodium 4-sulfophenyl 6-[(1-oxynonyl)-amino]hexanoate and 18.6% total solids was fed to the centrifuge. A cake consisting of 21% sodium 4-sulfophenyl 6-[(1-oxynonyl)-amino]hexanoate and 39% solids was recovered which represented a recovery of sodium 4-sulfophenyl 6-[(1-oxynonyl)-amino]hexanoate of 50%. Conversion of the starting material was very low, and the impurities resulting from the remaining starting material led to difficulty in obtaining a high recovery during the separation.

Example 17

Centrifuge conditions were similar to Example 16, except the centrifuge was fed at 900 lb/hr (6.8 kg/min). The slurry, which was fed at 155° C., was 20.9% total solids and 11.6% sodium 4-sulfophenyl 6-[(1-oxynonyl)-amino]hexanoate. The centrifuge produced a cake that was 27.8% sodium 4-sulfophenyl 6-[(1-oxynonyl)-amino]hexanoate, 49.3% solids, and 38.9% sulfolane. Recovery of sodium 4-sulfophenyl 6-[(1-oxynonyl)-amino]hexanoate was determined to be 77%, while removal of the sulfolane was calculated to be 82%. The higher feed rate in this example gave improved performance since the slurry was hitting the target with higher momentum and thus not sliding down the cake chute.

Example 18

A slurry consisting of 28.7% total solids and 21.3% sodium 4-sulfophenyl 6-[(1-oxynonyl)-amino]hexanoate in sulfolane was fed to the continuous vertical bowl centrifuge at 450 lb/hr and 150° C. The cake produced was 35.7% sodium 4-sulfophenyl 6-[(1-oxynonyl)-amino]hexanoate and 45.3% solids with 34.1% sulfolane, which represented 81.1% recovery of the sodium 4-sulfophenyl 6-[(1-oxynonyl)-amino]hexanoate.

TABLE 5

Examples 16–18: Continuous Vertical Bowl Centrifugation

| Example | | 16 | 17 | 18 |
|---|---|---|---|---|
| Acetic acid (wt %) | | 0.3 | 5.1 | 4.3 |
| Centrifuge temperature | | 120 | 110 | 122 |
| Average cooling rate | | 7 | 7 | 8 |
| Feed rate: | | 281–500 | 200–940 | 200–1170 |
| phenyl ester salt | Mean | 30 | 28.8 | 31.8 |
| in cake: | Range | 27–31 | 27–32 | 27–35 |
| Solids in cake: | Mean | 36 | 33.3 | 46.0 |
| | Range | 33–38 | 32–36 | 41–50 |
| Sulfolane in cake | Mean | 58 | 56 | 48 |
| Recovery of phenyl | Mean | 45.6 | 50.2 | 62.0 |
| ester salt: | Range | | 15–76 | 43–80 |
| phenyl ester salt | Mean | 7.4 | 8.8 | 12.1 |
| in centrate: | Range | | 5.1–12.5 | 7.7–15.1 |

V: Example 19

Continuous Sedicanter Centrifugation

Example 19

In Example 19, a Dorr-Oliver (Flottweg) sedicanter Model Z230-3 was evaluated. This centrifuge has an adjustable pool depth and continuously adjustable differential scroll speed. The machine required adjustments by the manufacturer e.g. replacement of specific seals and bearings as well as selection of an alternative lubrication fluid to run at temperatures exceeding 100° C. The internal bowl diameter was 230 mm with a total bowl length of 580 mm and a beach angle of 7.7 degrees. When the machine was run at 3000 G's of centrifugal force and a scroll differential speed of 4.5 rpm, a slurry consisting of 18% solids, 11.5% sodium 4-sulfophenyl 6-[(1-oxynonyl)-amino]hexanoate and 2.5% acetic acid was fed the centrifuge. The centrifuge produced a cake of 35.8% sodium 4-sulfophenyl 6-[(1-oxynonyl)-amino]hexanoate, 52.5% solids, and 40.4% sulfolane which represents 75.6% recovery of the sodium 4-sulfophenyl 6-[(1-oxynonyl)-amino]hexanoate. The centrate was found to contain 7.1% sodium 4-sulfophenyl 6-[(1-oxynonyl)-amino]hexanoate which can be recycled back to the reactors along with unreacted starting material.

TABLE 6

Example 19: Continuous Sedicanter Centrifugation

| Example | | 19 |
|---|---|---|
| Acetic acid (wt %) | | 2.5 |
| Centrifuge temperature | | 130 |
| Feed rate: | | 475 |
| phenyl ester salt in cake: | Mean | 35.8 |
| Solids in cake (wt. %): | Mean | 52.5 |
| Sulfolane in cake | Mean | 40.4 |
| Recovery of phenyl ester salt: | Mean | 75.6 |
| phenyl ester salt in centrate: | Mean | 3.7 |

It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference in their entirety.

The claimed invention is:

1. A process for isolating a phenyl ester salt from a mixture comprising a phenyl ester salt and sulfolane comprising the steps of:

(i) adjusting the temperature of a first mixture comprising a phenyl ester salt and sulfolane to a temperature of about 100–150° C. to form a second mixture comprising a solid phenyl ester salt and sulfolane; and (ii) separating the solid phenyl ester salt from the second mixture while maintaining the temperature of the mixture at a temperature of about 100–150° C.

2. A process of claim 1, wherein the first mixture is adjusted to a temperature of about 110–120° C., and the separating step comprises filtering or centrifuging the second mixture to separate the solid phenyl ester salt from the second mixture, while maintaining the temperature of the second mixture at a temperature of about 110–120° C.

3. A process of claim 1, wherein the first mixture is a crude reaction mixture resulting from a reaction to prepare the phenyl ester salt, the process further comprising the step of diluting the first or second mixture to provide a solid phenyl ester salt concentration of about 10–40 weight percent.

4. A process of claim 3, wherein the first or second mixture is diluted to provide a solid phenyl ester salt concentration of about 18–25 weight percent.

5. A process of claim 1, wherein the phenyl ester salt is a compound of formulae (I) or (II):

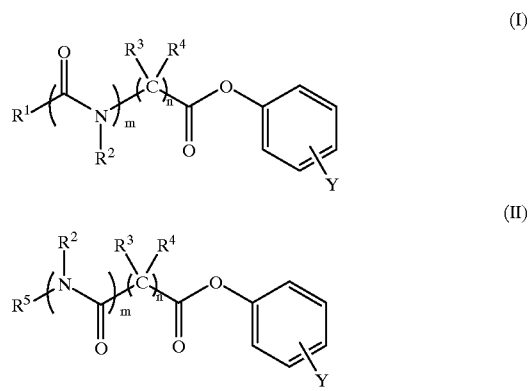

wherein $R^1$ is selected from $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl;

$R^2$ and $R^5$ are each independently selected from hydrogen, $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl, or in formula II, $R^2$ and $R^5$, together with the nitrogen carrying them, form a $C_3$–$C_{10}$ heterocycle;

$R^3$ and $R^4$ are each independently selected in each instance from hydrogen, $C_1$–$C_{10}$ alkyl, $C_2$–$C_{10}$ alkenyl, $C_2$–$C_{10}$ alkynyl, $C_3$–$C_{10}$ cycloalkyl, and $C_6$–$C_{10}$ aryl, or $R^3$ and $R^4$, together with the carbon carrying them, form a $C_3$–$C_{10}$ cycloalkyl;

Y is selected from $SO_3^-M^+$, $CO_2^-M^+$, $SO_4^-M^+$, and $N^+(R^6)_3X^-$;

M is selected from hydrogen, ammonium and alkali metal atom;

$R^6$ in each instance is a $C_1$–$C_4$ alkyl group;

X is a halide, hydroxide, methylsulfate, or acetate ion;

m is an integer from 0 to 1; and n is an integer from 0 to 20.

6. A process of claim 1, wherein the phenyl ester salt is a compound of formulae (I) or (II), wherein $R^1$ is selected from $C_6$–$C_{10}$ alkyl, and $C_6$–$C_{10}$ aryl;

$R^2$ is hydrogen;

$R^3$ in each instance is independently selected from hydrogen and methyl;

$R^4$ in each instance is independently selected from hydrogen and methyl;

$R^5$ is selected from hydrogen, $C_6$–$C_{10}$ alkyl, and $C_6$–$C_{10}$ aryl;

Y is selected from $SO_3^-M^+$, and $CO_2^-M^+$;

M is a sodium ion;

m is an integer from 0 to 1; and n is an integer from 0 to 6.

7. A process of claim 1, wherein the phenyl ester salt is selected from sodium 4-sulfophenyl-6-[(1-oxynonyl)-amino]hexanoate, sodium 4-(nonanoyloxy) benzenesulfonate, or sodium benzoyloxybenzenesulphonate.

8. A process for isolating a phenyl ester salt from a mixture comprising a phenyl ester salt and sulfolane comprising the steps of:

(i) adding a sufficient amount of at least one solvent to a mixture comprising a phenyl ester salt and sulfolane to decrease the viscosity or the density of the mixture, wherein the solvent which is added has a density less than about 1.20 g/cm³ at 100° C. or a viscosity of less than about 2.56 centipoise at 100° C., and wherein the phenyl ester salt may be a solid phenyl ester salt;

(ii) optionally, adjusting the temperature of the first mixture to form a second mixture comprising a solid phenyl ester salt; and (iii) separating the solid phenyl ester salt from the first or second mixture while maintaining the mixture at a temperature of about 100–150° C.

9. A process of claim 8, wherein the solvent is added in an amount of less than about 10 weight percent, based on the weight of the mixture containing the phenyl ester salt and sulfolane.

10. A process of claim 9, wherein the solvent is added in an amount of about 2 weight percent to about 4 weight percent, based on the weight of the mixture containing the phenyl ester salt and sulfolane.

11. A process of claim 9, wherein the solvent is selected from carboxylic acids, alkanes, ketones, or alcohols.

12. A process of claim 11, wherein the solvent is selected from acetic acid, propionic acid, pentanol, n-butyl alcohol, methyl propyl ketone, methyl isobutyl ketone, methyl isopropyl ketone, and heptane.

13. A process of claim 8, wherein the solvent is acetic acid or aqueous acetic acid.

14. A process of claim 13, wherein the solvent is added in an amount of less than about 10 weight percent, based on the weight of the mixture comprising the phenyl ester salt and sulfolane.

15. A process of claim 14, wherein the solvent is added in an amount of about 2 to about 4 weight percent, based on the weight of the mixture comprising the phenyl ester salt and sulfolane.

16. A process of claim 8, wherein during the addition step, the mixture is maintained at a temperature ranging from about 110–120° C.

17. A process of claim 8, wherein the solid phenyl ester salt is separated from the mixture prior to any substantial decomposition of the phenyl ester salt or the sulfolane.

18. A process of claim 8, wherein the phenyl ester salt is a compound of formulae (I) or (II):

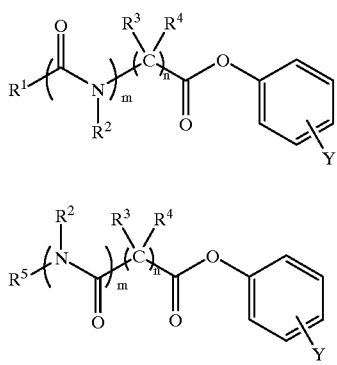

wherein
$R^1$ is selected from $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl;
$R^2$ and $R^5$ are each independently selected from hydrogen, $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl, or in formula II, $R^2$ and $R^5$, together with the nitrogen carrying them, form a $C_3$–$C_{10}$ heterocycle;
$R^3$ and $R^4$ are each independently selected in each instance from hydrogen, $C_1$–$C_{10}$ alkyl, $C_2$–$C_{10}$ alkenyl, $C_2$–$C_{10}$ alkynyl, $C_3$–$C_{10}$ cycloalkyl, and $C_6$–$C_{10}$ aryl, or $R^3$ and $R^4$, together with the carbon carrying them, form a $C_3$–$C_{10}$ cycloalkyl;
Y is selected from $SO_3^-M^+$, $CO_2^-M^+$, $SO_4^-M^+$, and $N^+(R^6)_3X^-$;
M is selected from hydrogen, ammonium and alkali metal atom;
$R^6$ in each instance is a $C_1$–$C_4$ alkyl group;
X is a halide, hydroxide, methylsulfate, or acetate ion;
m is an integer from 0 to 1; and
n is an integer from 0 to 20.

19. A process of claim 8, wherein the phenyl ester salt is a compound of formulae (I) or (II), wherein
$R^1$ is selected from $C_6$–$C_{10}$ alkyl, and $C_6$–$C_{10}$ aryl;
$R^2$ is hydrogen;
$R^3$ in each instance is independently selected from hydrogen and methyl;
$R^4$ in each instance is independently selected from hydrogen and methyl;
$R^5$ is selected from hydrogen, $C_6$–$C_{10}$ alkyl, and $C_6$–$C_{10}$ aryl;
Y is selected from $SO_3^-M^+$, and $CO_2^-M^+$;
M is a sodium ion;
m is an integer from 0 to 1; and
n is an integer from 0 to 6.

20. A process of claim 8, wherein the phenyl ester salt is selected from sodium 4-sulfophenyl-6-[(1-oxynonyl)-amino]hexanoate, sodium 4-(nonanoyloxy) benzenesulfonate, or sodium benzoyloxybenzenesulphonate.

21. A process for isolating a phenyl ester salt from a mixture comprising a phenyl ester salt and sulfolane comprising the steps of:

(i) adjusting the temperature of a first mixture comprising a phenyl ester salt and sulfolane to a temperature of about 100–150° C. to form a second mixture comprising a solid phenyl ester salt and sulfolane;

(ii) adding a sufficient amount of a solvent to the mixture comprising the phenyl ester salt and sulfolane to decrease the viscosity or the density of the mixture, wherein the solvent which is added has a density less than about 1.20 g/cm³ at 100° C. or a viscosity less than about 2.56 centipoise at 100° C.; and (iii) separating the solid phenyl ester salt from the second mixture while maintaining the mixture at a temperature of about 100–150° C., wherein steps (i), and (ii) may be performed in any order.

22. A process of claim 21, wherein the first mixture is a crude reaction mixture resulting from a reaction to prepare a phenyl ester salt, the process further comprising the step of diluting the first or second mixture to a solid phenyl ester salt concentration of about 10–40 weight percent.

23. A process of claim 21, wherein the solvent is acetic acid or aqueous acetic acid.

* * * * *